(12) United States Patent
Greaves et al.

(10) Patent No.: US 7,288,121 B2
(45) Date of Patent: *Oct. 30, 2007

(54) COMPOSITION COMPRISING AT LEAST ONE MIXED DYE COMPRISING AT LEAST ONE CHROMOPHORE CHOSEN FROM COMPOUNDS OF THE METHINE FAMILY AND/OR THE CARBONYL FAMILY, DYEING PROCESS AND KIT, AND MIXED DYES

(75) Inventors: Andrew Greaves, Montevrain (FR); Hervé David, Joinville le Pont (FR); Henri Samain, Bievres (FR)

(73) Assignee: L'Oreal S.A., Paris (FR)

( * ) Notice: Subject to any disclaimer, the term of this patent is extended or adjusted under 35 U.S.C. 154(b) by 335 days.

This patent is subject to a terminal disclaimer.

(21) Appl. No.: 11/066,467

(22) Filed: Feb. 28, 2005

(65) Prior Publication Data

US 2005/0251923 A1 Nov. 17, 2005

Related U.S. Application Data

(60) Provisional application No. 60/568,269, filed on May 6, 2004.

(30) Foreign Application Priority Data

Feb. 27, 2004 (FR) .................................. 04 50381
Jun. 25, 2004 (FR) .................................. 04 07021

(51) Int. Cl.
*A61K 7/13* (2006.01)

(52) U.S. Cl. ...................... 8/405; 8/406; 8/407; 8/410; 8/411; 8/423; 8/426; 8/437; 8/565; 8/566; 8/567; 8/568; 8/570; 8/573; 8/574; 8/608; 534/269.4; 548/301.7

(58) Field of Classification Search ............... 8/405, 8/406, 407, 410, 411, 423, 426, 437, 565, 8/566, 567, 568, 570, 573, 574, 608; 534/269.4; 548/301.7

See application file for complete search history.

(56) References Cited

U.S. PATENT DOCUMENTS

| 3,423,427 A | 1/1969 | Cescon et al. |
| 3,652,556 A | 3/1972 | Kühltau et al. |
| 3,995,088 A | 11/1976 | Garner et al. |
| 4,054,718 A | 10/1977 | Garner et al. |
| 4,670,385 A | 6/1987 | Babb et al. |
| 4,823,985 A | 4/1989 | Grollier et al. |
| 5,094,688 A | 3/1992 | Eckstein et al. |
| 5,097,034 A | 3/1992 | Eckstein |
| 5,132,438 A | 7/1992 | Bach et al. |
| 5,139,997 A | 8/1992 | Bach et al. |
| 5,708,151 A * | 1/1998 | Mockli ........................ 534/608 |
| 5,821,347 A | 10/1998 | Dannheim |
| 5,831,039 A | 11/1998 | Schumacher |
| 6,140,478 A | 10/2000 | Geiwiz et al. |
| 6,297,362 B1 | 10/2001 | Kunde et al. |
| 6,547,834 B1 | 4/2003 | Matsunaga et al. |
| 6,884,265 B2 | 4/2005 | Vidal et al. |
| 7,172,633 B2 * | 2/2007 | Samain et al. ................. 8/405 |
| 2003/0163879 A1 | 9/2003 | Brennan et al. |

FOREIGN PATENT DOCUMENTS

| BE | 702239 | 1/1969 |
| DE | 1 254 118 | 11/1967 |
| DE | 33 35 956 | 4/1985 |
| DE | 198 45 640 | 4/2000 |
| EP | 1 153 599 | 11/2001 |
| EP | 1 153 598 | 11/2004 |
| FR | 2 586 913 | 3/1987 |
| GB | 822 846 | 11/1959 |
| GB | 1 047 796 | 11/1966 |
| GB | 1 139 408 | 1/1969 |
| JP | A S40-021144 | 9/1965 |
| JP | A S41-004102 | 3/1966 |
| JP | A S53-139636 | 12/1978 |
| JP | A H05-345862 | 12/1993 |
| JP | A H09-111137 | 4/1997 |
| JP | A H05-318938 | 12/1997 |
| JP | A 2001-316230 | 11/2001 |
| JP | A 2001-316231 | 11/2001 |
| JP | A 2002-080332 | 3/2002 |
| WO | WO 02/78596 | 10/2002 |
| WO | WO 02/078596 | 10/2002 |
| WO | WO 03/18021 | 3/2003 |
| WO | WO 03/029359 | 4/2003 |
| WO | WO 03/30909 | 4/2003 |

OTHER PUBLICATIONS

STIC Search Report dated Mar. 21, 2007.*
English translation of the first page of JP A S40-021144 (Sep. 20, 1965).
English translation of the first page of JP A S41-004102 (Mar. 8, 1966).
English Language Derwent Abstract for JP A S53-139 636 (Dec. 6, 1978).
Journal of Medicinal Chemistry 43(9), 2000, 1892-1897.
English language Abstract for DE 33 35 956 (Apr. 18, 1985).
Search Report for priority application FR 04/50381 (Feb. 27, 2004).

* cited by examiner

*Primary Examiner*—Eisa Elhilo
(74) *Attorney, Agent, or Firm*—Finnegan, Henderson, Farabow, Garrett & Dunner LLP

(57) ABSTRACT

The present invention relates to a dye composition including at least one mixed dye containing at least one chromophore of methine or carbonyl type or their combinations. The invention furthermore relates to a process for dyeing keratin fibers, especially human keratin fibers, such as the hair, using the composition, and also to a suitable kit. The invention also relates to the abovementioned mixed dyes per se.

32 Claims, No Drawings

COMPOSITION COMPRISING AT LEAST ONE MIXED DYE COMPRISING AT LEAST ONE CHROMOPHORE CHOSEN FROM COMPOUNDS OF THE METHINE FAMILY AND/OR THE CARBONYL FAMILY, DYEING PROCESS AND KIT, AND MIXED DYES

This application claims benefit of U.S. Provisional Application No. 60/568,269, filed May 6, 2004, of French Application No. 04/50381, filed Feb. 27, 2004, and of French Application No. 04/107021, filed Jun. 25, 2004, all of which are herein incorporated by reference.

The present disclosure relates to a dye composition comprising one or more mixed dyes including at least one chromophore chosen from compounds of the methine and/or carbonyl families, and a process for dyeing keratin fibers, such as human keratin fibers, with the composition. The present disclosure also relates to mixed dyes per se.

It is known practice to dye keratin fibers, such as human keratin fibers and in particular human hair, with dye compositions containing direct dyes. These direct dye compounds are colored and coloring molecules that have an affinity for the keratin fibers. Well-known direct dyes include, for example, nitrobenzene, anthraquinone, and nitropyridine direct dyes, as well as azo, xanthene, acridine, azine, and triarylmethane dyes.

Direct dyes are usually applied to keratin fibers, and may be applied in combination with an oxidizing agent if simultaneous lightening of the fibers is desired. Once the action time has elapsed, the fibers are rinsed, optionally washed, and dried.

The colorations resulting from the use of direct dyes are temporary or semi-permanent. The nature of the interactions that bind the direct dyes to the keratin fiber, and their desorption from the surface and/or core of the fiber results in weak dyeing power and relatively poor wash-fastness and/or perspiration-fastness.

Another drawback associated with the use of direct dyes is that it is necessary in most cases to mix several dyes in order to obtain a particular color. However, each dye does not have the same affinity for the fiber. As a result, in many cases the coloration is heterogeneous and/or changes color over time e.g., after washing the fibers one or more times, exposing the fibers to sunlight, etc.

Accordingly, one aspect of the present disclosure is to provide direct dyes that do not have at least some of the drawbacks of the existing direct dyes.

Another aspect of the present disclosure is to provide direct dyes that can afford varied shades without the problem of color change over time.

Accordingly, disclosed herein is a dye composition comprising, in a medium suitable for dyeing, at least one mixed dye comprising at least two different chromophores, wherein the chromophores are chosen from compounds of the methine family, the carbonyl family, or combinations thereof. The chromophores are linked together via at least one linker group that stops delocalization of the electrons of each of the chromophores, with the proviso that the mixed dye composition does not comprise a mixed dye comprising two chromophores of the family of methines, at least one of which bears a quinolinium group, or a dye of the following formula:

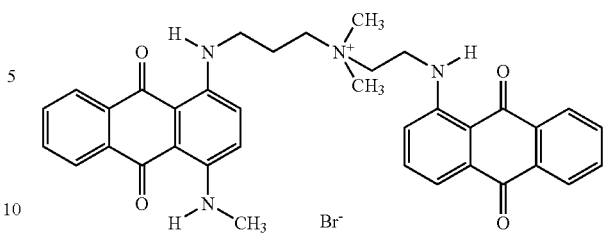

Another aspect of the present disclosure is a process for dyeing keratin fibers, in particular human keratin fibers, in which the above-mentioned dye composition is applied to the fibers, optionally in the presence of at least one oxidizing agent; the dye composition is left to act for a time that is sufficient to obtain the desired coloration; the fibers are optionally washed and/or rinsed; and then the fibers are either dried or left to dry.

The present disclosure also relates to mixed dyes comprising at least two different chromophores; the chromophores being chosen from compounds of the family of methines, from compounds of the carbonyl family or from their combinations; the chromophores being linked together via at least one linker group that stops delocalization of the electrons of each of the chromophores, with the exception of a mixed dye comprising two chromophores of the family of methines, at least one of which bears a quinolinium group and with the exception of a dye of the following formula:

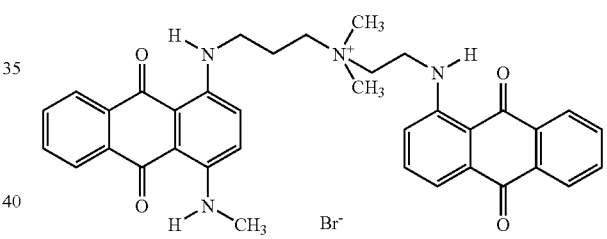

The mixed dyes and their addition salts according to the present disclosure, when present in a dye composition, make it possible to obtain strong, light-stable colors that are resistant to bad weather, washing, and perspiration, and show good fastness over time.

The above recited advantages of the present disclosure are non-limiting. Other characteristics and advantages of the present disclosure will emerge more clearly upon reading the description and the examples that follow.

As used herein, unless otherwise indicated, the expression "substituted alkyl, substituted aryl (or aromatic) or substituted heteroaryl (or heteroaromatic) radical" means an alkyl, aryl or heteroaryl radical bearing at least one radical chosen from: a hydroxyl radical; a halogen atom such as chlorine or fluorine; a linear or branched, substituted or unsubstituted $C_1$-$C_8$ alkoxy radical, such as a $C_1$-$C_4$ alkoxy radical; a linear or branched, substituted or unsubstituted monohydroxyalkoxy radical in which the alkyl portion is a $C_1$-$C_8$ alkyl radical, such as a $C_1$-$C_4$ alkyl radical; a linear or branched, substituted or unsubstituted $C_2$-$C_8$ polyhydroxyalkoxy radical, such as a $C_2$-$C_4$ polyhydroxyalkoxy radical; an amino radical substituted with at least one linear or branched, substituted or unsubstituted $C_1$-$C_8$ alkyl radical, such as a $C_1$-$C_6$, alkyl radical, that may be identical or different, and/or substituted with at least one optionally substituted aryl radical, such as a $C_6$ aryl radical; a thiol radical; a linear or branched, substituted or unsubstituted $C_1$-$C_8$ alkylthio radical, such as a $C_1$-$C_4$ alkylthio radical; a carboxylic radical in acid or salified form (in one embodiment, salified with an alkali metal or a substituted or unsubstituted ammonium); a linear or branched, substituted or unsubstituted alkoxycarbonyl radical in which the alkyl portion is a $C_1$-$C_8$ alkyl, such as a $C_1$-$C_4$ alkyl; an alkylamide radical in which the alkyl portion is a linear or branched, substituted or unsubstituted $C_1$-$C_8$ alkyl, such as a $C_1$-$C_4$ alkyl; an alkylcarbamyl radical in which the alkyl portion is a linear or branched, substituted or unsubstituted $C_1$-$C_8$ alkyl, such as a $C_1$-$C_4$ alkyl; a nitro radical; a sulfonyl radical; a linear or branched, substituted or unsubstituted $C_1$-$C_8$ alkysulfonyl radical, such as a $C_1$-$C_4$ alkylsulfonyl radical; a sulfonylamino radical; or an alkylsulfonylamido radical in which the alkyl portion is linear or branched, substituted or unsubstituted $C_1$-$C_8$ alkyl, such as a $C_1$-$C_4$ alkyl.

As used herein, unless otherwise specified, a heteroaromatic radical or heteroaryl radical corresponds to an aromatic radical in which at least one of the carbon atoms is replaced with a hetero atom, such as nitrogen, oxygen or sulfur.

Furthermore, when an alkyl or aryl radical or the alkyl or aryl portion of a radical substituting another radical is indicated, the radical itself may be substituted. More specifically, the radical can comprise one or more substituents chosen from: hydroxyl groups; amino groups; amino groups substituted with at least one linear or branched $C_1$-$C_4$ alkyl radical which may be identical or different, and may bear at least one hydroxyl group; and linear or branched $C_1$-$C_4$ alkoxy radicals that may bear at least one hydroxyl group.

When amino radicals bearing two substituents chosen from optionally substituted alkyl radicals are indicated, these alkyl radicals can also form a 5 or 6 membered ring, wherein at least one of the carbon atoms of the ring may be replaced with at least one nitrogen, oxygen, or sulfur atoms.

As used herein, unless otherwise indicated the end points delimiting the extent of a range of values are included in the specified range of values.

Additionally, since the mixed dyes according to the present disclosure are cationic, their counterion(s) is (are) chosen from cosmetically acceptable anions, of a mineral or organic nature. Examples of anions of a mineral nature include halides such as chlorides or bromides; hydroxides; sulfates; hydrogen sulfates; carbonates; and hydrogen carbonates.

Examples of anions of organic nature include anions such as acetate; citrate; tartrate; alkyl sulfates having a $C_1$-$C_6$ linear or branched alkyl portion, such as methosulfate or ethosulfate ion; alkylsulfonates having a $C_1$-$C_6$ linear or branched alkyl portion; and arylsulfonates, wherein the aryl portion of the arylsulfonate may be substituted with one or more $C_1$-$C_4$ alkyl radicals.

The mixed dyes present in the composition according to the invention will now be described.

As indicated previously, the mixed dyes comprise at least two different chromophores; the chromophores being chosen from compounds of the methine family, the carbonyl family, or from combinations thereof. Further, the chromophores are linked together via at least one linker group that stops delocalization of the electrons of each of the chromophores.

In one aspect of this disclosure at least one of the chromophores of the mixed dye bears at least one cationic charge.

As used herein, unless otherwise specified, the term "chromophore" means a radical derived from a dye, i.e., a radical of a molecule that absorbs in the visible range from 400 to 800 nm. It should be further noted that this absorbance of the dye does not require either any prior oxidation of the dye, or any association with (an)other chemical species.

Where chromophores are referred to as being different, this means that at least two of them, for example all of them, differ in their chemical structure. Such chromophores may be derived from different families or from the same family, provided that they have different chemical structures.

According to one embodiment of the present disclosure, the mixed dye comprises two to four chromophores. In another embodiment, the mixed dye comprises two to three chromophores, for example, two chromophores.

When the dye comprises three or more chromophores, at least one of these chromophores should be different from the others.

In another aspect of the invention, the at least one chromophore, which is cationic in nature, is chosen from chromophores comprising at least one quaternized nitrogen atom.

Furthermore, the aforementioned cationic charge(s) may or may not be engaged in a ring.

In another aspect of the present disclosure at least one of the chromophores of the mixed dye contains at least one cationic charge, and in some embodiments, only one cationic charge. In yet another aspect of the present disclosure, each chromophore comprises at least one cationic charge. In some embodiments the chromophore contains only one cationic charge.

In still another aspect of the present disclosure, the mixed dye has an overall cationic charge under the conditions of use of this mixed dye.

The mixed dye according to the present disclosure may thus comprise, in at least one embodiment, at least one chromophore from the methine family.

Regarding the chromophores of the methine family that may be used herein, these chromophores may, for example, be compounds comprising at least one sequence chosen from >C=C< and —N=C<, the two atoms of which are not simultaneously engaged in a ring. It is pointed out, however, that one of the nitrogen or carbon atoms of the sequences may be engaged in a ring.

For example, the chromophores of the methine family may be derived from chromophores of methine, azomethine, mono- and di-arylmethane, indamine (or diphenylamine), indophenol, indoaniline, carbocyanin, azacarbocyanin and isomers thereof, diazacarbocyanin and isomers thereof, tetraazacarbocyanin or hemicyanin type.

In one non-limiting embodiment, the methine family chromophore corresponds to formula (I) below, and the tautomeric forms thereof.

Formula I

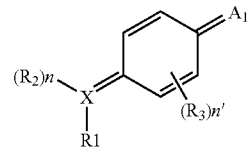

wherein:

$R_1$ and $R_2$ may be identical or different, and are chosen from a hydrogen atom; a $C_6$-$C_{30}$ aryl radical; a ($C_1$-$C_8$) alkylaryl radical wherein the aryl portion may be substituted with at least one identical or different group such as hydroxyl groups, linear or branched, substituted or unsubstituted $C_1$-$C_4$ alkoxy groups, amino groups, amino groups substituted with at least one linear or branched $C_1$-$C_4$ alkyl radical, which may be identical or different and may optionally bear at least one hydroxyl group, and halogen atoms, such as chlorine, and a heterocyclic radical chosen, for example, from thiophene, furan, piperonyl, indole, indoline, pyridine, carbazole, dehydroquinoline and chromone heterocycles;

$R_1$ and $R_2$ cannot simultaneously represent either an aromatic radical or a heteroaromatic radical;

$R_3$, which may be identical or different, is chosen from a hydrogen atom; a linear or branched, optionally substituted $C_1$-$C_8$ alkyl radical; an optionally substituted $C_6$-$C_{30}$ aryl radical; an amino radical; an amino radical substituted with at least one linear or branched $C_1$-$C_4$ alkyl radical, optionally bearing at least one hydroxyl group; a hydroxyl group; a linear or branched $C_1$-$C_8$ alkoxy radical, optionally bearing at least one hydroxyl group, a $C_1$-$C_4$ alkoxy group; or a halogen atom such as chlorine;

X is chosen from a nitrogen atom and a carbon atom;

n is equal to 0 when X is a nitrogen atom, and n is equal to 1 when X is a carbon atom;

n' is equal to 4;

$A_1$ is chosen from an amino group; an amino group substituted with at least one identical or different, linear or branched $C_1$-$C_8$ alkyl radical that may bear at least one hydroxyl group, an ammonium group $N^+(R_4)_2$, wherein $R_4$, which may be identical or different, is chosen from an optionally substituted $C_1$-$C_8$ alkyl radical; a $C_6$ aryl radical, which may be substituted, for example with at least one hydroxyl group, halogen atoms such as chlorine or fluorine, nitro groups, cyano groups, linear or branched $C_1$-$C_4$ alkoxy groups, linear or branched $C_1$-$C_4$ monohydroxyalkoxy groups, linear or branched $C_2$-$C_4$ polyhydroxyalkoxy groups, amino groups that may be unsubstituted or substituted with at least one linear or branched, identical or different $C_1$-$C_4$ alkyl or $C_1$-$C_4$ hydroxyalkyl radicals.

The chromophore may be linked to the linker group via the group $A_1$, via one of the radicals $R_1$, $R_2$, $R_3$ or $R_4$, or directly to the (hetero)aromatic ring(s). In the latter case, the radical $R_3$ represents a single bond between the chromophore and the linker group.

In one non limiting embodiment, when $R_1$ or $R_2$ represents a $C_6$ aryl radical, this radical may be substituted, for example with at least one group chosen from hydroxyl groups; amino groups; amino groups substituted with one or more identical or different $C_1$-$C_8$ alkyl radicals that may bear at least one group chosen from hydroxyl groups; halogen atoms; at least one $C_1$-$C_{12}$ alkylsulfonamido radical (alkyl-$SO_2$—NH—); at least one $C_1$-$C_{12}$ alkylsulfamoyl radical (alkyl-NH—$SO_2$—); at least one acyloxy radical in which the alkyl portion is $C_1$-$C_{12}$; and an alkoxycarbonyl radical in which the alkyl portion is $C_1$-$C_{12}$; at least one carboxyl radical.

Chromophores that are also suitable for use herein are those of formula II) below and the tautomeric forms thereof:

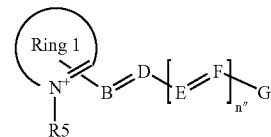

Formula 2 wherein:

B, D, E and F may be identical or different, and are chosen from a nitrogen atom and a group C—$R_6$, wherein each $R_6$ may be identical or different, and is chosen from a hydrogen atom; a $C_1$-$C_8$ alkyl radical which is optionally substituted, for example with at least one hydroxyl; a linear or branched $C_1$-$C_4$ alkoxy radical; an amino radical; an amino radical substituted with at least one linear or branched $C_1$-$C_4$ alkyl radical, which may be identical or different, optionally bearing at least one hydroxyl group; an optionally substituted $C_6$ aryl radical; and an optionally substituted 5- to 12-membered heteroaryl radical;

n" is 0 or 1;

G is chosen from Ring 4, defined below, or from the residues

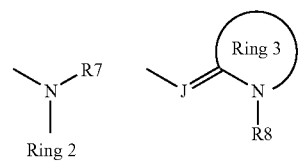

wherein:

$R_5$ and $R_8$ are chosen from, independently of each other, linear or branched, optionally substituted $C_1$-$C_8$ alkyl radicals; and optionally substituted benzyl radicals;

$R_7$ is chosen from a hydrogen atom; a $C_1$-$C_8$ alkyl radical which is optionally substituted, for example, with at least one hydroxyl; a linear or branched $C_1$-$C_4$ alkoxy radical; an amino radical; an amino radical substituted with at least one linear or branched $C_1$-$C_4$ alkyl radical, which may be identical or different, optionally bearing at least one hydroxyl group; an optionally substituted $C_6$ aryl radical; and an optionally substituted $C_2$-$C_{12}$ heteroaryl radical;

J is chosen from a nitrogen atom and a group C—$R_9$; wherein $R_9$ has the same meaning as $R_6$;

Ring 1 is chosen from 5- to 12-membered heteroaromatic radicals comprising at least one nitrogen atom and bearing at least one cationic charge on a nitrogen atom and optionally comprising at least one other hetero atom chosen from nitrogen, oxygen and sulfur, the radicals being optionally substituted with at least one entity chosen from at least one linear or branched, substituted or unsubstituted $C_1$-$C_8$ alkyl radical; at least one linear or branched, substituted or unsubstituted $C_1$-$C_8$ alkoxy radical; at least one amino radical; at least one amino radical substituted with at least one linear or branched $C_1$-$C_8$ alkyl group, which may be identical or different, optionally bearing at least one hydroxyl group; at least one $C_5$-$C_6$ aromatic radical; at least one hydroxyl group; an alkoxycarbonyl group; a nitro group; a cyano group; a $C_1$-$C_{12}$ alkylsulfonamido group (alkyl-$SO_2$—NH—); and a $C_1$-$C_{12}$ alkylsulfamoyl group (alkyl-NH—$SO_2$—);

Ring 2 is chosen from $C_6$-$C_{12}$ aromatic radicals; 5- to 12-membered heteroaromatic radicals, comprising at least one hetero atom chosen from nitrogen, oxygen and sulfur; the radicals being optionally substituted with at least one linear or branched $C_1$-$C_8$ alkyl radical; at least one linear or branched $C_1$-$C_8$ alkoxy radical; at least one amino radical; at least one amino radical substituted with at least one linear or branched $C_1$-$C_8$ alkyl group, which may be identical or different, optionally bearing at least one hydroxyl group; at least one (hetero)aromatic radical, which may be, for example, 5- to 6-membered; and at least one hydroxyl group. In at least one embodiment, Ring 2 represents a $C_6$-$C_{30}$ aromatic radical, optionally substituted as indicated above;

Ring 3 is chosen from 5- or 6-membered heteroaromatic radicals comprising at least one hetero atom chosen from nitrogen, oxygen and sulfur; wherein the radicals are optionally substituted with at least one linear or branched $C_1$-$C_8$ alkyl radical; at least one linear or branched $C_1$-$C_8$ alkoxy radical; at least one amino radical; at least one amino radical substituted with at least one linear or branched $C_1$-$C_8$ alkyl group, which may be identical or different, optionally bearing at least one hydroxyl group; at least one $C_5$-$C_6$ aromatic radical; at least one hydroxyl group; an alkoxycarbonyl group; a nitro group; a cyano group; a $C_1$-$C_{12}$ alkylsulfonamido group (alkyl-$SO_2$—NH—); and a $C_1$-$C_{12}$ alkylsulfamoyl group (alkyl-NH—$SO_2$—);

Ring 4 is chosen from $C_6$-$C_{12}$ aromatic radicals or 5- to 12-membered heteroaromatic radicals comprising at least one hetero atom chosen from nitrogen, oxygen and/or sulfur; wherein the radicals are optionally substituted with at least one linear or branched $C_1$-$C_8$ alkyl radical; at least one linear or branched $C_1$-$C_8$ alkoxy radical; at least one amino radical; at least one amino radical substituted with at least one linear or branched $C_1$-$C_8$ alkyl group, which may be identical or different, optionally bearing at least one hydroxyl group; at least one (hetero)aromatic radical, which is, for example, 5- or 6-membered; and at least one hydroxyl group;

with the overall provisos that when n" is 1 and G is Ring 4, then B, D, E and F do not simultaneously represent a nitrogen atom and when n" is 0 and G is Ring 4, then B and D do not simultaneously represent a nitrogen atom.

Further, the chromophore may be linked to the linker group via one of the radicals $R_5$, $R_6$, $R_7$, $R_8$ and $R_9$ or via a ring. In the latter case, the radical borne by the ring represents a single bond between the chromophore and the linking agent.

Formula (II) includes the positional isomers corresponding to the various possibilities of insertion of the bond of B onto the ring 1 relative to the quaternized nitrogen atom.

According to one embodiment of the present disclosure, the chromophore of the methine family is chosen from the compounds of the following formulae and the tautomeric forms thereof:

Indamines (diphenylamine) 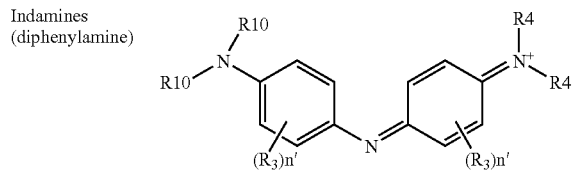

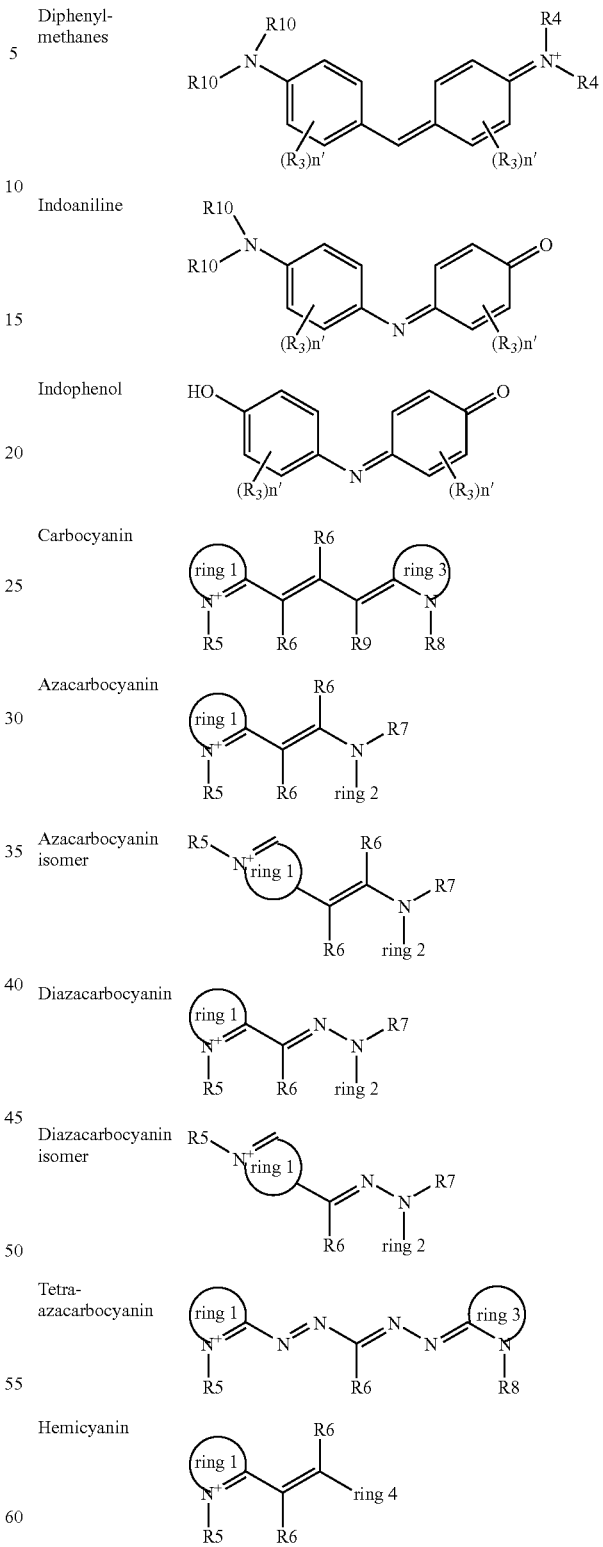

wherein, in the above formulae:

$R_{10}$, which may be identical or different, is chosen from a hydrogen atom, an optionally substituted $C_1$-$C_8$ alkyl radical; and a $C_6$ aryl radical which is optionally substituted, for example with at least one entity chosen from hydroxyl groups, halogen atoms such as Cl or F, nitro groups, cyano groups, linear or branched $C_1$-$C_4$ alkoxy groups, linear or branched $C_1$-$C_4$ monohydroxyalkoxy groups, linear or branched $C_2$-$C_4$ polyhydroxyalkoxy groups, and amino groups that may be unsubstituted or substituted with at least one linear or branched $C_1$-$C_4$ alkyl or $C_1$-$C_4$ hydroxyalkyl radicals, which may be identical or different;

The groups and radicals $R_1$, $R_3$, $R_4$, $R_5$, $R_6$, $R_7$, $R_8$, $R_9$, Ring 1, Ring 2, Ring 3 and Ring 4 are defined as set forth above. n' is also defined as set forth above.

In one aspect of the present disclosure the Ring 1 group is chosen from an imidazolium, pyridinium or indolinium ring, optionally substituted as indicated previously.

In another aspect of the present disclosure, the Ring 3 group is chosen from an imidazole, pyridine or indoline ring, optionally substituted as indicated previously.

In a further aspect of the present disclosure, the Ring 2 group represents a $C_6$ aromatic radical, optionally substituted as indicated previously.

In another aspect of the present disclosure, the Ring 4 group represents a $C_6$ aromatic radical, optionally substituted as indicated previously.

The chromophore may be linked to the linker group via one of the groups $R_3$, $R_4$, $R_5$, $R_6$, $R_7$, $R_8$ and $R_{10}$ or via an aromatic or heteroaromatic ring. In the case of attachment via a ring, the radical borne on the ring represents a single bond between the chromophore and the linker group.

In a further aspect of the present disclosure, the chromophore is chosen from the compounds of formula (II), for example, from diazacarbocyanins, isomers thereof, and hemicyanins. In this aspect, $R_6$, which may be identical or different, is chosen from a hydrogen atom; a $C_1$-$C_8$ alkyl radical optionally substituted, for example, with at least one hydroxyl; an optionally substituted $C_6$ aryl radical; n=0; G has a structure chosen from Ring 4 and —N($R_7$)-Ring 2. wherein $R_7$ is chosen from a hydrogen atom; a $C_1$-$C_8$ alkyl radical, which is optionally substituted, for example with at least one hydroxyl; and Ring 2 and Ring 4, which may be identical or different, are chosen from optionally substituted $C_6$ aromatic radicals.

In this aspect of the disclosure, the chromophore and the linker group are linked via the radical $R_5$.

The above described chromophores may be prepared according to the teaching of the following patent applications and patents: GB822846; DE1254118; GB1047796; U.S. Pat. Nos. 3,652,556; 3,423,427; BE702239; GB702240; U.S. Pat. Nos. 3,995,088; 4,054,718; 4,670,385; 5,094,688; 4,097,034.

Suitable chromophores of the carbonyl family that may be used in the present disclosure include but are not limited to, chromophores derived from dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole, coumarin, such as those derived from dyes chosen from acridone, benzoquinone, anthraquinone, naphthoquinone, benzanthrone, indanthrone, flavone, quinacridone, indigoid, thioindigo, naphthalimide, diketopyrrolopyrrole and coumarin.

More specifically, the chromophore of the carbonyl family is represented by formula (III) below:

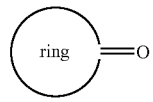

wherein the ring represents a 5- or 6-membered ring, at least one of the ring members of which is optionally replaced with a hetero atom chosen from oxygen, nitrogen and sulfur, or with an additional carbonyl function. The ring may be substituted with at least one radicals chosen from: optionally substituted linear or branched $C_1$-$C_8$ alkyl radicals; with at least one hydroxyl radical; halogen atoms such as chlorine; and nitro, cyano, amino or alkylamino groups. The ring may be optionally fused with at least one $C_6$ aromatic ring, wherein the at least one aromatic ring may itself be fused with at least one aromatic ring, at least one of the carbon atoms of which is optionally replaced with at least one hetero atom chosen from oxygen, nitrogen and sulfur.

Moreover, the chromophore of the carbonyl family may be linked to the linker group via one of the radicals substituting the rings or via a ring. In the latter case, the radical borne by the ring represents a single bond between the chromophore and the linking agent.

In accordance with one embodiment of the present disclosure, the chromophore of the carbonyl family is represented by one of the following formulae, as well as the tautomeric forms thereof:

Acridones

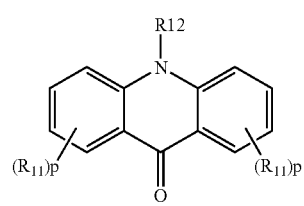

-continued
Anthraquinones
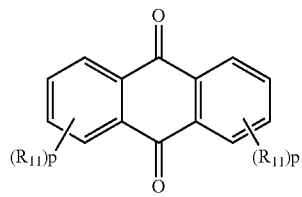
Benzanthrones
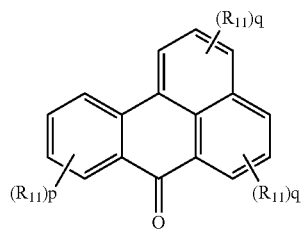
Benzoquinones
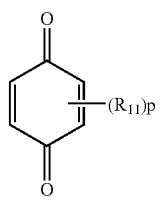
Flavones
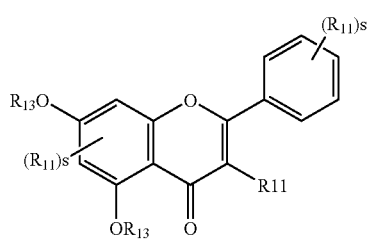
Indanthrones
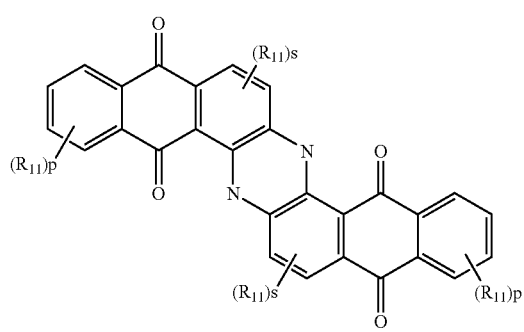
Naphthoquinones
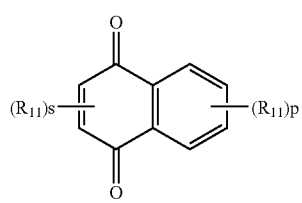

-continued

Quinacridones
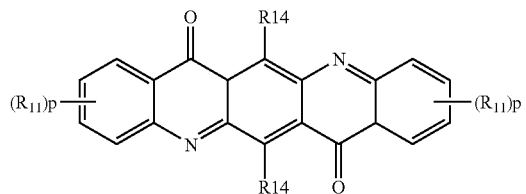

Indigoids
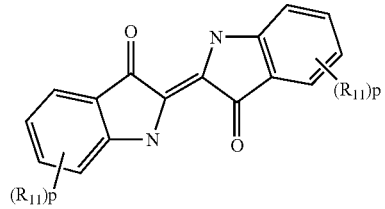

Thioindigos
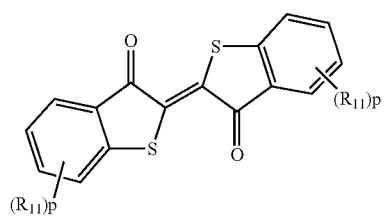

Naphthalimides
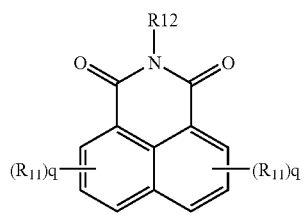

Diketopyrrolopyrroles
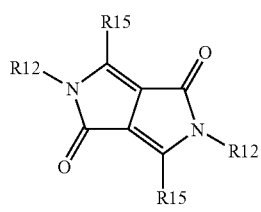

Coumarins
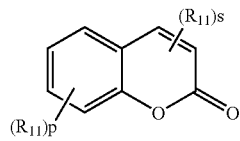

wherein:

$R_{11}$, $R_{12}$, and $R_{14}$, which may be identical or different, are chosen from a hydrogen atom; linear or branched, optionally substituted $C_1$-$C_8$ alkyl radicals; hydroxyl groups; linear or branched $C_1$-$C_8$ alkoxy radicals; amino radicals; and amino radicals substituted with at least one linear or branched $C_1$-$C_8$ alkyl radical, which may be identical or different and may bear at least one hydroxyl group; a halogen atom such as chlorine or fluorine; a nitro group; and a cyano group;

$R_{13}$ is chosen from a hydrogen atom and a linear or branched, optionally substituted $C_1$-$C_8$ alkyl radical;

$R_{15}$, which may be identical or different, is chosen from a $C_6$ aryl radical, which is optionally substituted, for example with at least one hydroxyl; at least one amino group; at least one amino group substituted with at least one linear or branched $C_1$-$C_8$ alkyl radical, which may be identical or different, optionally bearing at least one hydroxyl; at least one linear or branched $C_1$-$C_8$ alkoxy group optionally bearing at least one hydroxyl; at least one halogen atom such as chlorine or fluorine; at least one nitro group; and at least one cyano group;

p is equal to 4; q is equal to 3; r is equal to 5; s is equal to 2.

As mentioned previously, the chromophores of the mixed dye are linked together by means of at least one linker group that stops delocalization of the electrons of each of the chromophores. The chromophore may be linked to the linker group via one of the radicals $R_{11}$, $R_{12}$, $R_{13}$, $R_{14}$ or $R_{15}$ or via one of the aromatic or heteroaromatic rings. In the latter case, the radical borne by the ring represents a single bond between the chromophore and the linking agent.

Thus, the linker group comprises an atom or a group of atoms that isolate(s) each of the chromophores of the mixed dye.

In one aspect of the present disclosure, the bond between the radical and the linking agent is made by means of a nitrogen or oxygen atom.

It should also be noted that the linking agent may be cationic or non-cationic.

Furthermore, the linking agent may be divalent, trivalent or tetravalent.

According to one non-limiting embodiment of the present disclosure, the linker group is chosen from a linear or branched $C_1$-$C_{20}$ hydrocarbon-based chain, such as a $C_1$-$C_{12}$ hydrocarbon-based chain, for example, an alkyl chain, wherein at least one of the carbon atoms of the chain may be replaced with a hetero atom such as sulfur, nitrogen or oxygen, so long as the chain does not comprise two adjacent hetero atoms; or may be replaced with a saturated or unsaturated 5- or 6-membered heterocycle, such as a 6-membered heterocycle comprising at least two nitrogen atoms; the hydrocarbon-based chain may be unsaturated or contain an arylene radical; the linker group may also be chosen from an arylene radical; from a divalent terephthalamide radical; and from a divalent or trivalent radical, for example of triazine type.

In one embodiment, the linker group corresponds to a linear or branched $C_1$-$C_{20}$ alkyl chain, such as a $C_1$-$C_{12}$ alkyl chain, at least one of the carbon atoms of which may be replaced with a saturated or unsaturated 5- or 6-membered heterocycle, which in one embodiment comprises at least two nitrogen atoms.

Examples of mixed dyes according to the present disclosure that comprise two chromophores, include for example the following mixed dyes:

methine—linker group—methine
methine—linker group—carbonyl
carbonyl—linker group—carbonyl.

As mixed dyes according to the present disclosure, mention may be made of the dyes comprising two chromophores from the family of the methines, more specifically those from the family of the diazacarbocyanins and their isomers, the hemicyanins, with the exception of mixed dyes comprising two chromophores from the family of the methines, at least one of which bears a quinolinium group, and of a dye of the following formula:

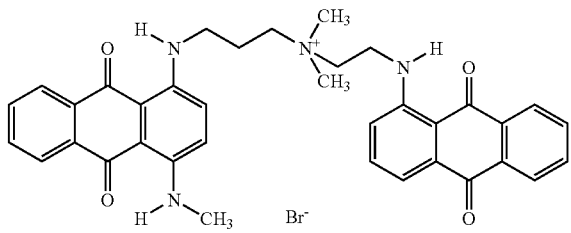

The following formula is a non-limiting example of a mixed dye according to the present disclosure, and its addition salts:

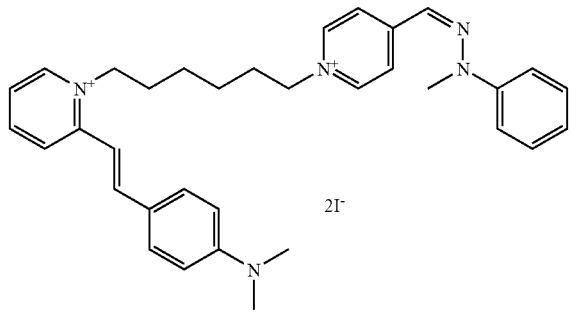

The mixed dyes of the invention may be prepared according to chemical reactions that are known per se, starting with functionalized chromophores capable of reacting with the chosen linker group.

For example, when the linker group is a triazine group, and the chromophore comprises a reactive amino, OH or SH group, the synthesis may be performed, for example, according to the schemes below:

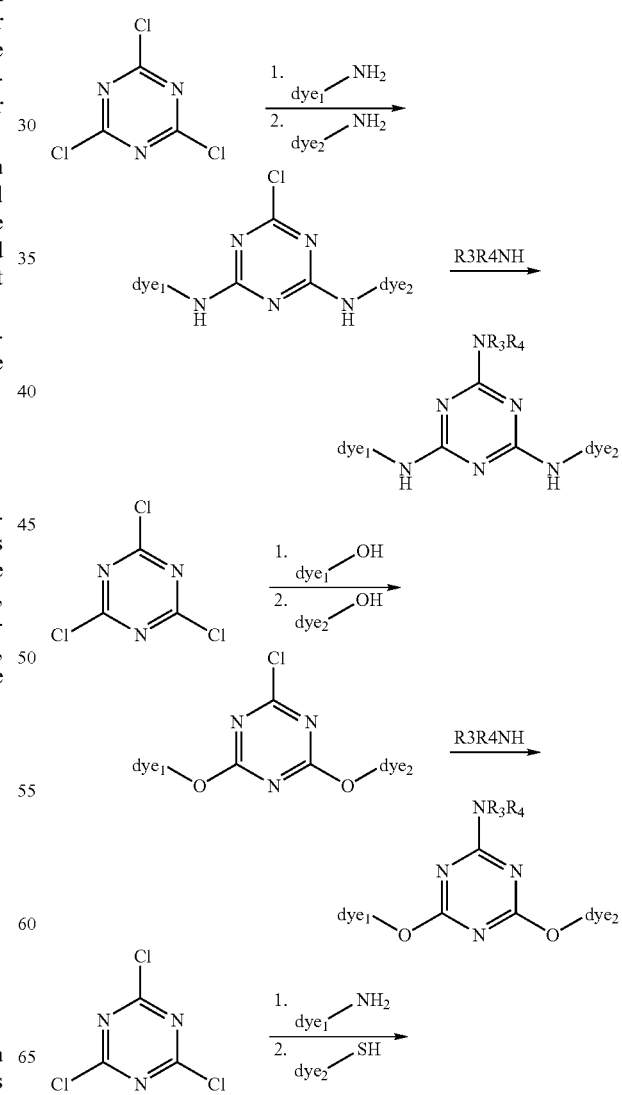

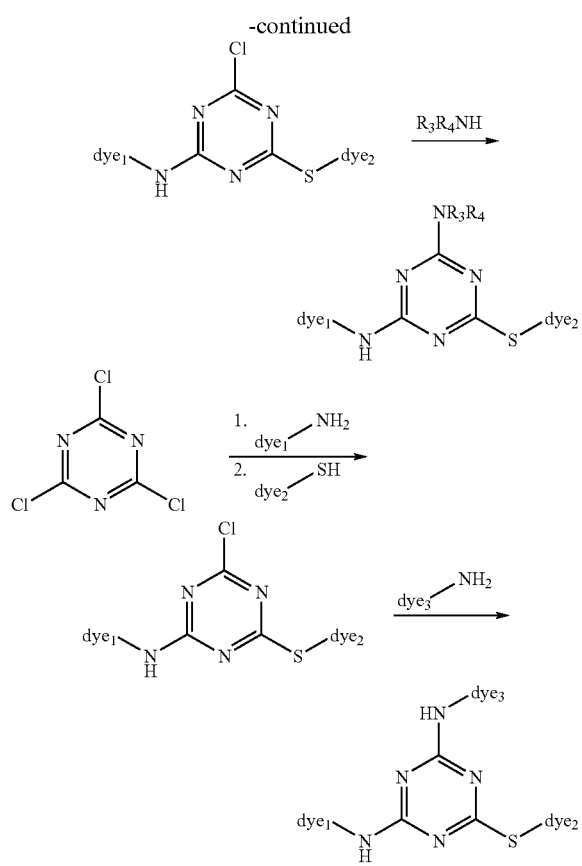

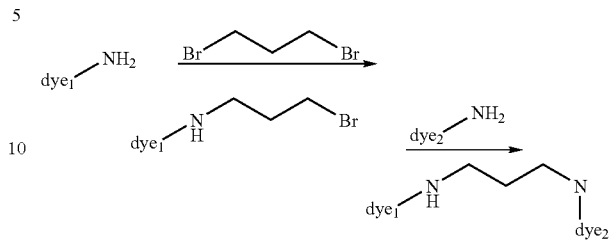

According to a first step, a first chromophore is mixed with the compound capable of forming the linker group, for example trichlorotriazine. When this reaction is complete, a second chromophore is added to the reaction medium. This sequence may be repeated as many times as there are reactive groups on the compound capable of forming the linker group.

For the preparation of a mixed dye Dye1-linker group-Dye2, the molar ratio of the linker group relative to Dye1 ranges from 10:1 to 0.5:1 and in one embodiment is equal to 1:1. This ratio may be modified when more than one linker group or several chromophores are used.

The reaction temperature generally ranges from −100° C. to +130° C., for instance from −5° C. to 100° C. The reaction time depends on the reactivity of the species present and on the reaction temperature. In general, the reaction time is from 10 minutes to 8 hours, for instance from 30 minutes to 4 hours.

The reaction may also be performed in water and/or in one or more organic solvents.

Several publications describe the reaction for the chemical combination between two identical chromophores. See for example, the disclosures of ISBN 0901956759, WO 02/78596, DE 198 45 640 and U.S. Pat. No. 5,708,151.

In addition, the reactions of a linker group with two different compounds, which may or may not be dyes, have been described in the literature. See for example, WO 03/029359, DE 33 35 956, WO 03/30909, WO 03/18021, Journal of Medicinal Chemistry 43(9), 2000, 1892-97; Chemiker Zeitung 117(7-8), 1987, 241-5.

In another non-limiting embodiment of the present disclosure, the mixed dye may be obtained according to the following reaction scheme:

According to a first step, a first chromophore is mixed with the compound capable of forming the linker group, for example dibromopropane. When this reaction is complete, a second chromophore is added to the reaction medium. This sequence may be repeated as many times as there are reactive groups on the compound capable of forming the linker group.

For the preparation of a mixed dye Dye1-linker group-Dye2, the molar ratio of the linker group relative to Dye1 generally ranges from 10:1 to 0.1:1, and may be equal to 0.5:1. This ratio may be modified when more than one linker group or several chromophores are used.

The reaction temperature is generally from −100° C. to +30° C. and for instance from −5° C. to 100° C. The reaction time depends on the reactivity of the species present and on the reaction temperature. In general, the reaction time is from 10 minutes to 24 hours, and may be, for example, from 30 minutes to 4 hours.

In one embodiment, the pH of the reaction mixture may range from 2 to 12.

The reaction may be performed in water and/or in one or more organic solvents.

The composition according to the present disclosure may comprise a content of mixed dye ranging from 0.001% to 20% by weight, such as from 0.005% to 10% by weight or from 0.01% to 5% by weight, relative to the total weight of the composition.

The dye composition according to the present disclosure may contain one or more additional direct dyes other than the mixed dye(s) described above. For example, direct dyes conventionally used in the field of dyeing keratin fibers, such as human keratin fibers, may be used. In this respect, mention may be made of nitrobenzene dyes, azo direct dyes and methine direct dyes. These additional direct dyes may be of nonionic, anionic or cationic nature, for example, of cationic nature.

According to another non-limiting embodiment of the present disclosure, the dye composition comprises a content of each of the additional direct dyes ranging from 0.001% to 10% by weight relative to the total weight of the dye composition.

The dye composition of the invention may also contain one or more oxidation bases and/or one or more couplers conventionally used for dyeing keratin fibers, and especially human keratin fibers.

Among the oxidation bases that may be mentioned are para-phenylenediamines, bis(phenyl)alkylenediamines, para-aminophenols, eortho-aminophenols and heterocyclic-bases, and the addition salts thereof.

The oxidation base(s) present in the composition of the present disclosure can each be present, for example, in an amount from 0.001% to 10% by weight relative to the total weight of the composition, such as from 0.005% to 6% by weight relative to the total weight of the dye composition.

Examples of couplers that may be used, non-limiting mention may be made of, for example, meta-phenylenediamines, meta-aminophenols, meta-diphenols, naphthalene-based couplers and heterocyclic couplers, and the addition salts thereof.

In the dye composition as disclosed herein, the coupler(s) may each be, for example, present in an amount from 0.001% to 10% by weight, such as from 0.005% to 6% by weight relative to the total weight of the dye composition.

The addition salts of the oxidation bases and of the couplers that may be used in the context of the present dislclosure may be chosen from the addition salts with an acid, such as the hydrochlorides, hydrobromides, sulfates, citrates, succinates, tartrates, lactates, tosylates, benzenesulfonates, phosphates and acetates, and the addition salts with a base, such as sodium hydroxide, potassium hydroxide, ammonia, amines or alkanolamines.

One non-limiting example of the medium that is suitable for dyeing, also known as the dye support, is a cosmetic medium that generally comprises water or a mixture of water and at least one organic solvent to dissolve the compounds that would not be sufficiently soluble in water.

Non-limiting examples of organic solvents that may be mentioned include $C_1$-$C_4$ alkanols, such as ethanol and isopropanol; polyols and polyol ethers, for instance 2-butoxyethanol, propylene glycol, propylene glycol monomethyl ether, diethylene glycol monoethyl and monomethyl ether, and aromatic alcohols, for instance benzyl alcohol or phenoxyethanol, and mixtures thereof.

The solvents are present, for example, in proportions from 1% to 40% by weight relative to the total weight of the dye composition, such as from 5% to 30% by weight.

The dye composition in accordance with the present disclosure may also comprise various adjuvants conventionally used in compositions for dyeing keratin fibers, human keratin, or hair. Non limiting examples of suitable adjuvants include, for example: anionic, cationic, nonionic, amphoteric or zwitterionic surfactants or mixtures thereof; anionic, cationic, nonionic, amphoteric or zwitterionic polymers or mixtures thereof; mineral or organic thickeners, including anionic, cationic, nonionic and amphoteric associative polymeric thickeners; antioxidants; penetrating agents; sequestering agents; fragrances; buffers; dispersants; conditioning agents, for instance volatile or non-volatile, modified or unmodified silicones; film-forming agents; ceramides, pseudoceramides; preserving agents; opacifiers, etc.

The above adjuvants are, for example, present in an amount for each of them ranging from 0.01% to 20% by weight individually relative to the weight of the composition.

The composition of the invention may also contain at least one oxidizing agent.

The oxidizing agents conventionally used for the oxidation dyeing of keratin fibers such as human keratin fibers are, for example, hydrogen peroxide, urea peroxide, alkali metal bromates or ferricyanides, persalts such as perborates and persulfates of alkali metals or of alkaline-earth metals, such as sodium, potassium or magnesium, alone or as mixtures, peracids and oxidase enzymes, among which mention may be made of peroxidases, two-electron oxidoreductases such as uricases, and four-electron oxygenases, for instance laccases. In one embodiment of the present disclosure, hydrogen peroxide is used.

The composition of the invention may also comprise at least one alkaline agent, which may be chosen from those conventionally used in cosmetics.

Among these alkaline agents, non-limiting examples that may be mentioned include: aqueous ammonia; alkaline carbonates; alkanolamines such as monoethanolamine; diethanolamine; and triethanolamine, and derivatives thereof; sodium hydroxide; potassium hydroxide; and compounds of formula (A) below:

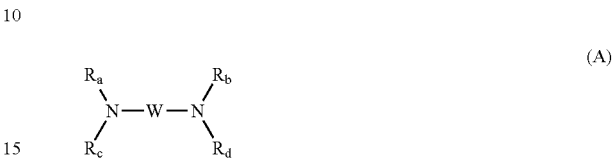

in which W is a propylene residue optionally substituted with a functional group chosen from a hydroxyl group or a $C_1$-$C_4$ alkyl radical; $R_a$, $R_b$, $R_c$ and $R_d$, which may be identical or different, are chosen from a hydrogen atom or a $C_1$-$C_4$ alkyl or $C_1$-$C_4$ hydroxyalkyl radical.

The pH of the dye composition of the present disclosure may range from, for example, 8 to 11.

Needless to say, a person skilled in the art will take care to select the optional additional compound(s) such that the advantageous properties intrinsically associated with the composition according to the present disclosure are not, or are not substantially, adversely affected by the envisaged addition(s).

The dye composition according to the present disclosure may be in various forms, such as in the form of liquids, creams or gels, or in any other form that is suitable for dyeing keratin fibers, such as human keratin fibers, particularly hair.

The process of the present disclosure is a process in which the composition according to one embodiment of the present disclosure is applied to the wet or dry fibers.

According to another embodiment, the composition applied to the keratin fibers does not comprise any oxidizing agent. This variant is suitable when the dye composition comprises at least one mixed dye according to the disclosure and optionally at least one additional direct dye.

In yet another embodiment of the present disclosure, the process is performed with at least one oxidizing agent. This embodiment is suitable irrespective of the nature of the dyes present (mixed dye, additional direct dye, oxidation bases and/or couplers). Such a process allows lightening of the treated fiber to be obtained.

According to this embodiment, the oxidizing agent may be added to the dye composition at the time of use, or it may be used starting with an oxidizing composition comprising it, which is applied simultaneously with or sequentially to the dye composition comprising the mixed dye. In this latter case, the oxidizing agent is present in a composition different from the one comprising the mixed dye.

According to another non limiting embodiment, the dye composition comprising the mixed dye is mixed, for example, at the time of use, with a composition comprising, in a medium that is suitable for dyeing, at least one oxidizing agent, this oxidizing agent being present in an amount that is sufficient to obtain the desired lightening.

The mixture obtained is then applied to the keratin fibers.

After an action time that is sufficient to obtain the desired coloration, usually ranging from 3 to 50 minutes, such as from 5 to 30 minutes, the keratin fibers are preferably rinsed, washed with shampoo, rinsed again and then dried or left to dry.

The composition may be conventionally left to act at a temperature ranging from 15 to 80° C., such as from 15 to 40° C.

The oxidizing composition may also contain various adjuvants conventionally used in compositions for dyeing keratin fibers, especially human keratin fibers, and as defined above.

In one non-limiting embodiment of the present disclosure, the pH of the oxidizing composition containing the oxidizing agent is such that, after mixing with the dye composition, the pH of the resulting composition applied to the keratin fibers (i.e., in other words, the ready-to-use composition) ranges from 7 to 12, such as from 8 to 11. It may be adjusted to the desired value by means of acidifying or basifying agents.

Among the acidifying agents, examples that may be mentioned include mineral or organic acids, for instance hydrochloric acid, orthophosphoric acid, sulfuric acid or acetic acid.

As regards the basifying compounds, reference may be made to the list given hereinabove.

The ready-to-use composition may be in various forms, such as in the form of liquids, creams or gels, or in any other form that is suitable for dyeing keratin fibers and especially human keratin fibers, such as hair.

Another aspect of the disclosure is a a multi-compartment device in which at least one first compartment comprises a dye composition comprising at least one mixed dye as described above, optionally at least one additional direct dye different from the mixed dye, optionally at least one oxidation base, optionally at least one coupler, and another compartment comprising an oxidizing agent.

It should be noted that the mixed dye, optionally the additional direct dye, the oxidation base(s) and the coupler(s) may be in the same compartment or in several compartments; the same compartment possibly comprising only one type of dye (mixed dye, additional direct dye or oxidation dye) or a combination of several of these dyes.

The aforementioned device may be equipped with a means for applying the desired mixture to the fibers to be treated, such as the devices described in patent FR 2 586 913.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific example are reported as precisely as possible. Any numerical value, however, inherently contain certain errors necessarily resulting from the standard deviation found in their respective testing measurements.

The following examples are intended to illustrate the invention in a non-limiting manner.

EXAMPLES

Example 1

Synthesis of the Mixed Dye

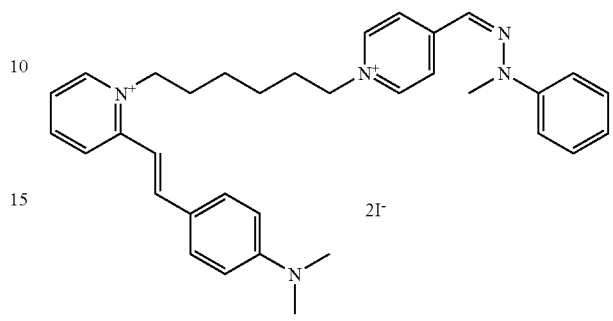

Reaction scheme:

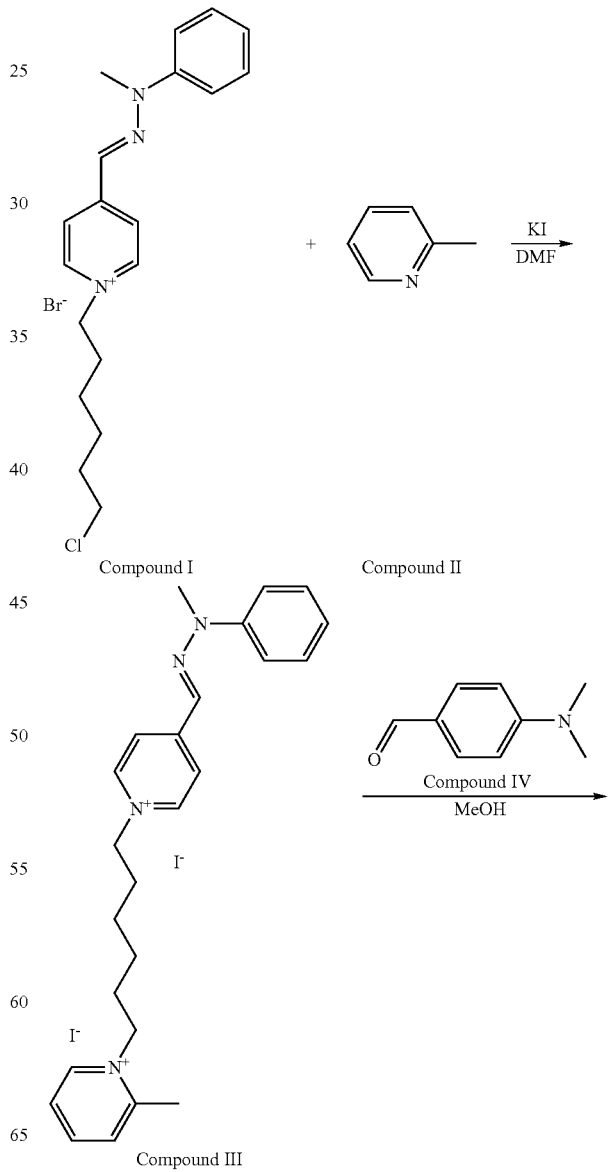

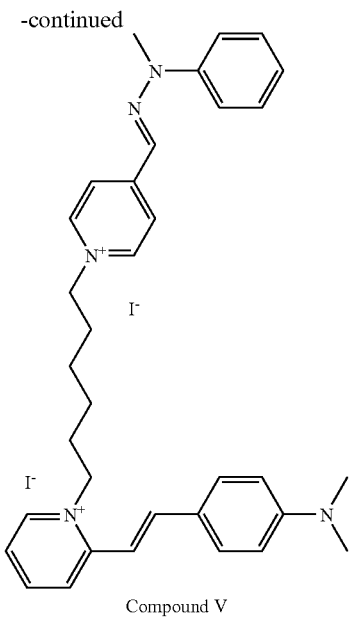

Compound V

Process:

Step 1

A three-necked flask was charged successively with 1.2 g of hydrazone (compound I), 10 ml of dimethylformamide (DMF), 10 ml of picoline (compound II) and 0.96 g of KI, and then this initial charge was stirred for 24 hours at 110° C.

The reaction mixture was subsequently precipitated from diisopropyl ether.

This resulted in an oil, which was solidified in an acetone/ethyl acetate (1/1) mixture.

The analyses (NMR, mass spectrum) were in accordance with the proposed structure of the intermediate (compound III).

Step 2

1.4 g of the intermediate (compound III), 2 molar equivalents of aldehyde (compound IV), 2 ml of pyrrolidine and 40 ml of methanol were placed with stirring in a three-necked flask for 5 hours.

The precipitate formed was filtered off and then washed repeatedly with isopropanol.

This gave an orange powder.

The NMR analyses were in accordance with the structure of the expected product (compound V); for example, mass spectrum: ES+ 260; UV-Vis spectrum: lambda max 425 nm.

Example 2

Dyeing Applications

1/Dye Composition

The mixed dye obtained in the previous example was formulated at $6.46 \times 10^{-4}$ mol % in the dye composition A.

| Composition A | |
|---|---|
| (50/50 $C_8/C_{10}$) alkyl polyglucoside as a buffered aqueous 60% solution | 10 g |
| Benzyl alcohol | 10 g |
| Polyethylene glycol 400 containing 8 ethylene oxide units | 12 g |
| Mixed dye (compound V) | $6.46 \times 10^{-4}$ mol |
| 20.5% aqueous ammonia | 10 g |
| Demineralized water | qs 100 g |

At the time of use, composition A was mixed with 20 volumes aqueous hydrogen peroxide solution (weight for weight, pH=3.5).

The pH of the dye composition after mixing was between 9.5 and 10.

The mixture was then applied to locks of natural grey hair (NG) or permanent-waved grey hair (PWG) containing 90% white hairs.

The action time on the locks was 20 minutes at room temperature.

The locks were then washed with shampoo.

Dyed locks were obtained.

2/Shampoo-Fastness

Permed locks of hair dyed according to the protocol from paragraph 1/of Example 2 with, on the one hand, the composition according to the disclosure comprising the mixed dye and, on the other hand, a comparative composition comprising the equimolar mixture of the constituent dyes, were subjected to six shampooings, with intermediate drying between two shampooings.

Orange dye:

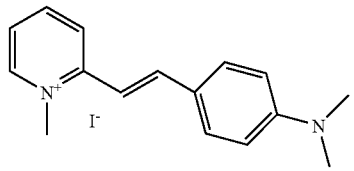

Yellow dye:

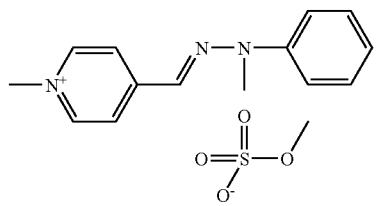

The color after the six shampoo washes was compared with the initial color of the dyed lock, visually and by colorimetric measurement.

The shampoo fastness was measured on natural dyed hair and on dyed permanent-waved hair according to the $\Delta E$ formula below, using the L*a*b* values measured on each type of lock before ($L_0^* a_0^* b_0^*$) and after ($L_1^* a_1^* b_1^*$) the 6 shampoo washes (Minolta CM2002 calorimeter, illuminant D65-10° CSI).

$$\Delta E = \sqrt{(L_1^* - L_0^*)^2 + (a_1^* - a_0^*)^2 + (b_1^* - b_0^*)^2}$$

The colorimetric results are collated in Tables 1 and 2 below.

TABLE 1

Composition according to the invention:

| | L* | a* | b* | Degradation |
|---|---|---|---|---|
| PWG/before shampooing | 46.18 | 32.71 | 47.95 | 5.72 |
| PWG/after shampooing | 49.08 | 28.00 | 49.40 | |

TABLE 2

Comparative composition:

| Type of hair | L* | a* | b* | Degradation |
|---|---|---|---|---|
| PWG/before shampooing | 49.38 | 33.54 | 51.85 | 14.34 |
| PWG/after shampooing | 56.53 | 21.12 | 52.24 | |

The mixed dye exhibited a better resistance to repeated shampooing than the physical mixture of the two dyes.

What is claimed is:

1. A dye composition comprising, in a medium suitable for dyeing keratin fibers, at least one mixed dye comprising at least two different chromophores, wherein the chromophores are chosen from compounds of the methine family, from compounds of the carbonyl family, and from combinations thereof; and further wherein the at least two chromophores are linked together via at least one linker group that stops delocalization of the electrons of each of the chromophores;

with the proviso that the composition does not comprise a mixed dye comprising two chromophores of the methine family, at least one of which bears a quinolinium group, or a dye of the following formula:

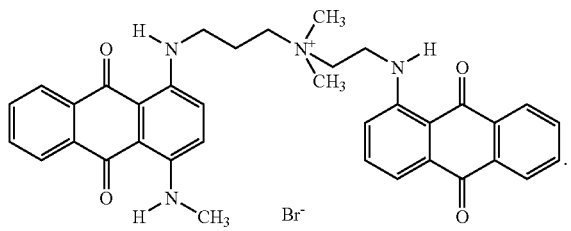

2. The dye composition of claim 1, wherein at least one of the two different chromophores bears at least one cationic charge.

3. The dye composition of claim 1, wherein the chromophores absorb in the visible range from 400 to 800 nm.

4. The dye composition of claim 1, wherein the at least one mixed dye comprises two to four chromophores.

5. The dye composition according to claim 1, wherein the at least one mixed dye comprises two chromophores.

6. The dye composition of claim 2, wherein the at least one chromophore bearing at least one cationic charge comprises at least one quaternized nitrogen atom.

7. The dye composition of claim 1, wherein the chromophores of the methine family are chosen from compounds comprising at least one sequence chosen from >C=C< and —N=C<, the two atoms of which are not simultaneously engaged in a ring; and further wherein one of the nitrogen or carbon atoms of the sequences may be engaged in a ring.

8. The dye composition of claim 7, wherein the chromophores of the methine family are chosen from radicals derived from chromophores of the family of methines, azomethines, mono- and diarylmethanes, indamines, indoanilines, indophenols, indoanilines, carbocyanins, azacarbocyanins and isomers thereof, diazacarbocyanins and isomers thereof, tetraazacarbocyanins and hemicyanins, and isomers thereof.

9. The dye composition of claim 7, wherein the chromophores of the methine family are radicals derived from chromophores of formula (I) and the tautomeric forms thereof:

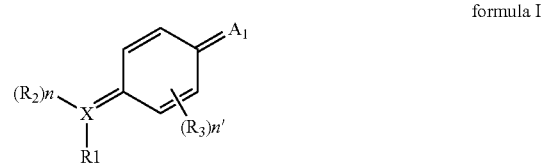

formula I or chromophores of formula (II) and the tautomeric forms thereof:

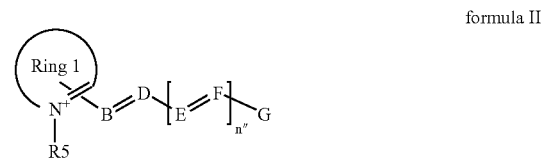

formula II wherein in formula (I):

$R_1$ and $R_2$, which may be identical or different, are chosen from: a hydrogen atom; $C_6$-$C_{30}$ aryl radicals; ($C_1$-$C_8$) alkylaryl radicals wherein the aryl portion is optionally substituted, and heterocyclic radicals;

wherein $R_1$ and $R_2$ cannot simultaneously be aromatic radicals or heteroaromatic radicals;

$R_3$, which may be identical or different, is chosen from: a hydrogen atom; a linear or branched, optionally substituted $C_1$-$C_8$ alkyl radical; an optionally substituted $C_6$-$C_{30}$ aryl radical; an amino radical; an amino radical substituted with at least one linear or branched $C_1$-$C_4$ alkyl radical that optionally bears at least one hydroxyl group; a hydroxyl group; a linear or branched $C_1$-$C_8$ alkoxy radical that optionally bears at least one hydroxyl group; a $C_1$-$C_4$ alkoxy group; or a halogen atom;

X is chosen from a nitrogen atom and a carbon atom;

n is 0 when X is a nitrogen atom, and n is 1 when X is a carbon atom;

n' is equal to 4;

$A_1$ is chosen from: an amino group; an amino group substituted with at least one linear or branched $C_1$-$C_8$ alkyl radical, which may be identical or different and may optionally bear at least one hydroxyl group; an ammonium group $N^+(R_4)_2$, wherein $R_4$, which may be identical or different, is chosen from an optionally substituted $C_1$-$C_8$ alkyl radical; and a $C_6$ aryl radical that is optionally substituted;

wherein in formula (II):

B, D, E and F may be identical or different and are chosen from a nitrogen atom and a group C—$R_6$, wherein $R_6$ may be identical or different and is chosen from: a hydrogen atom; an optionally substituted $C_1$-$C_8$ alkyl radical; a linear or branched $C_1$-$C_4$ alkoxy radical; an amino radical; an amino radical substituted with at least one linear or branched $C_1$-$C_4$ alkyl radical, which may be identical or different and may optionally bear at least one hydroxyl group; an optionally substituted $C_6$ aryl radical; and an optionally substituted 5- to 12-membered heteroaryl radical;

n" is 0 or 1;

G is chosen from Ring 4, defined below, or from the residues:

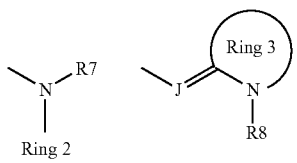

wherein:

R$_5$ and R$_8$ are chosen from, independently of each other, linear or branched, optionally substituted $C_1$-$C_8$ alkyl radicals and optionally substituted benzyl radicals;

R$_7$ is chosen from: a hydrogen atom; an optionally substituted $C_1$-$C_8$ alkyl radical; a linear or branched $C_1$-$C_4$ alkoxy radical; an amino radical; an amino radical substituted with at least one linear or branched $C_1$-$C_4$ alkyl radical that may be identical or different and may optionally bear at least one hydroxyl group; an optionally substituted $C_6$ aryl radical; or an optionally substituted $C_2$-$C_{12}$ heteroaryl radical;

J is chosen from a nitrogen atom and a group C—R$_9$; wherein R$_9$ is defined as R$_6$ above;

Ring 1 is chosen from 5- to 12-membered heteroaromatic radicals comprising at least one nitrogen atom, bearing at least one cationic charge on a nitrogen atom, and optionally comprising at least one other hetero atom chosen from nitrogen, oxygen and sulfur; wherein said heteroaromatic radicals are optionally substituted with at least one entity chosen from at least one linear or branched, substituted or unsubstituted $C_1$-$C_8$ alkyl radical; at least one linear or branched, substituted or unsubstituted $C_1$-$C_8$ alkoxy radical; at least one amino radical; at least one amino radical substituted with at least one linear or branched $C_1$-$C_8$ alkyl group that may be identical or different and may optionally bear at least one hydroxyl group; at least one $C_5$-$C_6$ aromatic radical; at least one hydroxyl group; an alkoxycarbonyl group; a nitro group; a cyano group; a $C_1$-$C_{12}$ alkylsulfonamido group (alkyl-SO$_2$—NH—); and a $C_1$-$C_{12}$ alkylsulfamoyl group (alkyl-NH—SO$_2$—);

Ring 2 is chosen from: $C_6$-$C_{12}$ aromatic radicals; 5- to 12-membered heteroaromatic radicals comprising at least one hetero atom chosen from nitrogen, oxygen and sulfur; wherein said heteroaromatic radicals are optionally substituted with at least one entity chosen from at least one linear or branched $C_1$-$C_8$ alkyl radical; at least one linear or branched $C_1$-$C_8$ alkoxy radical; at least one amino radical; at least one amino radical substituted with at least one linear or branched $C_1$-$C_8$ alkyl group that may be identical or different and may optionally bear at least one hydroxyl group; at least one (hetero)aromatic radical; and at least one hydroxyl group;

Ring 3 is chosen from 5- or 6-membered heteroaromatic radicals comprising at least one hetero atom chosen from nitrogen, oxygen and sulfur; wherein said heteroaromatic radicals are optionally substituted with at least one entity chosen from at least one linear or branched $C_1$-$C_8$ alkyl radical; at least one linear or branched $C_1$-$C_8$ alkoxy radical; at least one amino radical; at least one amino radical substituted with at least one linear or branched $C_1$-$C_8$ alkyl group that may be identical or different and may optionally bear at least one hydroxyl group; at least one $C_5$-$C_6$ aromatic radical; at least one hydroxyl group; an alkoxycarbonyl group; a nitro group; a cyano group; a $C_1$-$C_{12}$ alkylsulfonamido group (alkyl-SO$_2$—NH—); and a $C_1$-$C_{12}$ alkylsulfamoyl group (alkyl-NH—SO$_2$—);

Ring 4 is chosen from $C_6$-$C_{12}$ aromatic radicals; and 5- to 12-membered heteroaromatic radicals, comprising at least one hetero atom chosen from nitrogen, oxygen and sulfur; wherein said heteroaromatic radicals are optionally substituted with at least one entity chosen from at least one linear or branched $C_1$-$C_8$ alkyl radical; at least one linear or branched $C_1$-$C_8$ alkoxy radical; at least one amino radical; at least one amino radical substituted with at least one linear or branched $C_1$-$C_8$ alkyl group that may be identical or different and may optionally bear at least one hydroxyl group; at least one (hetero)aromatic radical; and at least one hydroxyl group;

with the overall provisos that:

when n" is 1 and G is Ring 4, B, D, E and F are not simultaneously a nitrogen atom; and when n" is 0 and G is Ring 4, then B and D are not simultaneously a nitrogen atom.

10. The dye composition of claim 9, wherein said aryl portion of said ($C_1$ to $C_8$)alkylaryl radical in the definition of R$_1$ and R$_2$ is substituted with at least one group, which may be identical or different, chosen from hydroxyl groups, linear or branched, substituted or unsubstituted $C_1$-$C_4$ alkoxy groups, amino groups, amino groups substituted with at least one linear or branched, $C_1$-$C_4$ alkyl radical that may be identical or different and may optionally bear at least one hydroxyl group, and halogen atoms.

11. The dye composition of claim 9, wherein the heterocyclic radicals in the definition of R$_1$ and R$_2$ are chosen from thiophene, furan, piperonyl, indole, indoline, pyridine, carbazole, dehydroquinoline and chromone heterocycles.

12. The dye composition of claim 9, wherein in the definition of A$_1$ the $C_6$ aryl radical is substituted with at least one entity chosen from hydroxyl groups, halogen atoms, nitro groups, cyano groups, linear or branched $C_1$-$C_4$ alkoxy groups, linear or branched $C_1$-$C_4$ monohydroxyalkoxy groups, linear or branched $C_2$-$C_4$ polyhydroxyalkoxy groups, or amino groups that are unsubstituted or substituted with at least one linear or branched $C_1$-$C_4$ alkyl or hydroxyalkyl radicals, which may be identical or different.

13. The dye composition of claim 9, wherein in the definitions of R$_6$ and R$_7$, the $C_1$-$C_8$ alkyl radical is substituted with at least one hydroxyl group.

14. The dye composition of claim 1, wherein the mixed dye comprises at least one chromophore chosen from compounds of the carbonyl family.

15. The dye composition of claim 14, wherein the chromophore chosen from compounds of the carbonyl family is chosen from radicals derived from dyes of the family of acridones, benzoquinones, anthraquinones, naphthoquinones, benzanthrones, anthranthrones, pyranthrones, pyrazolanthrones, pyrimidinoanthrones, flavanthrones, idanthrones, flavones, (iso)violanthrones, isoindolinones, benzimidazolones, isoquinolinones, anthrapyridones, pyrazoloquinazolones, perinones, quinacridones, quinophthalones, indigoids, thioindigos, naphthalimides, anthrapyrimidines, diketopyrrolo-pyrroles and coumarins.

16. The dye composition of claim 14, wherein the chromophore chosen from compounds of the carbonyl family is a radical derived from dyes of formula (III) below:

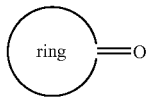

wherein in formula (III)
the ring is a 5- or 6-membered ring, at least one of the ring members of which may be replaced with a hetero atom chosen from oxygen, nitrogen and sulfur, or with an additional carbonyl function; said ring being optionally substituted with at least one entity chosen from: optionally substituted linear or branched $C_1$-$C_8$ alkyl radicals; at least one hydroxyl radical; at least one halogen atom; and at least one group chosen from nitro, cyano, amino and alkylamino groups; said ring being optionally fused with at least one $C_6$ aromatic ring, wherein the at least one $C_6$ ring is itself optionally fused with at least one aromatic ring, at least one of the carbon atoms of which is optionally replaced with at least one hetero atoms chosen from oxygen, nitrogen and sulfur.

17. The dye composition of claim 1, wherein the at least one linker group is cationic or non-cationic.

18. The dye composition of claim 1, wherein the at least one linker group is chosen from:
a linear or branched $C_1$-$C_{20}$ hydrocarbon-based chain wherein at least one of the carbon atoms of the hydrocarbon-based chain may be replaced with a hetero atom or with a saturated or unsaturated $C_5$-$C_6$ heterocycle, said hydrocarbon-based chain optionally being unsaturated or containing an arylene radical
an arylene radical,
a divalent terephthalamide radical, or
a divalent or trivalent radical.

19. The dye composition of claim 1, wherein the at least one mixed dye is present in an amount ranging from 0.001% to 20% by weight, relative to the total weight of the composition.

20. The dye composition of claim 19, wherein said at least one mixed dye is present in an amount ranging from 0.01% to 5% by weight relative to the total weight of the composition.

21. The dye composition of claim 1, wherein the composition comprises at least one additional direct dye other than said at least one mixed dye.

22. The dye composition of claim 21, wherein the content of each additional direct dye ranges from 0.001% to 10% by weight relative to the total weight of the dye composition.

23. The dye composition of claim 1, further comprising at least one oxidation base chosen from para-phenylenediamines, bis(phenyl)alkylenediamines, para-aminophenols, ortho-aminophenols and heterocyclic bases, and the addition salts thereof.

24. The dye composition of claim 1, further comprising at least one coupler chosen from meta-phenylenediamines, meta-aminophenols, meta-diphenols, naphthalene-based couplers and heterocyclic couplers, and the addition salts thereof.

25. The dye composition of claim 23, wherein the content of each oxidation base ranges from 0.001% to 10% by weight relative to the total weight of the dye composition, and the content of each coupler ranges from 0.001% to 10% by weight relative to the total weight of the dye composition.

26. The dye composition of claim 1, wherein the composition further comprises at least one oxidizing agent.

27. The dye composition of claim 26, where the at least one oxidizing agent is chosen from hydrogen peroxide, alkali metal peroxides, alkaline-earth metal peroxides, urea peroxide, alkali metal bromates, alkali metal ferricyanides, persalts, and enzymes.

28. The dye composition of claim 1, wherein the pH ranges from 8 to 11.

29. A process for dyeing keratin fibers, comprising:
a) applying a dye composition to wet or dry fibers, optionally in the presence of at least one oxidizing agent,
b) leaving the composition on the fibers for a time that is sufficient to obtain a desired coloration,
c) optionally rinsing the fibers,
d) washing and rinsing the fibers, and
e) drying the fibers or leaving the fibers to dry,
wherein said dye composition comprises, in a medium suitable for dyeing keratin fibers, at least one mixed dye comprising at least two different chromophores, wherein the chromophores are chosen from compounds of the methine family, from compounds of the carbonyl family, and from combinations thereof; and further wherein the at least two chromophores are linked together via at least one linker group that stops delocalization of the electrons of each of the chromophores;
with the proviso that the composition does not comprise a mixed dye comprising two chromophores of the methine family, at least one of which bears a quinolinium group, or a dye of the following formula:

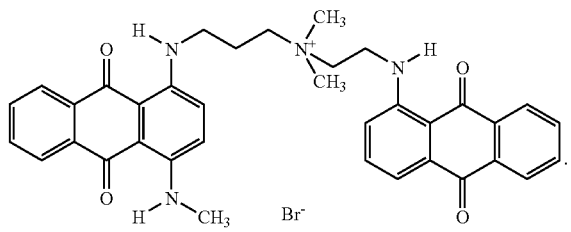

30. A multi-compartment device comprising
at least one first compartment comprising a dye composition comprising, in a medium suitable for dyeing keratin fibers, at least one mixed dye comprising at least two different chromophores, wherein the chromophores are chosen from compounds of the methine family, from compounds of the carbonyl family, and from combinations thereof; and further wherein the at least two chromophores are linked together via at least one linker group that stops delocalization of the electrons of each of the chromophores;
with the proviso that the composition does not comprise a mixed dye comprising two chromophores of the methine family, at least one of which bears a quinolinium group, or a dye of the following formula:

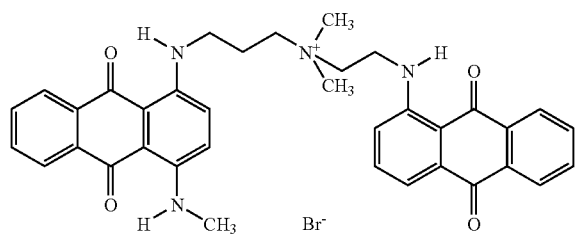

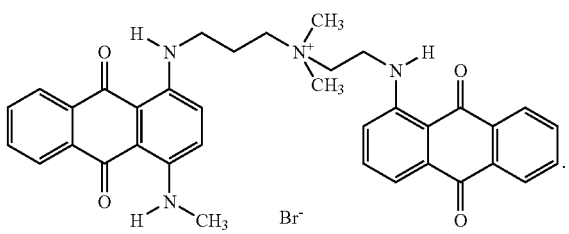

at least one second compartment comprising at least one oxidizing agent;
wherein at least one of the compartments further optionally comprises at least one of
at least one additional direct dye different from the mixed dye,
at least one oxidation base, and
at least one coupler.

31. A mixed dye comprising at least two different chromophores, wherein the chromophores are chosen from compounds of the methine family, from compounds of the carbonyl family, and from combinations thereof; and further wherein the at least two chromophores are linked together via at least one linker group that stops delocalization of the electrons of each of the chromophores;
with the exception of a mixed dye comprising two chromophores of the family of methines, at least one of which bears a quinolinium group and a dye of the following formula:

32. The dye composition of claim 1, wherein the chromophore has the following formula, and the addition salts thereof:

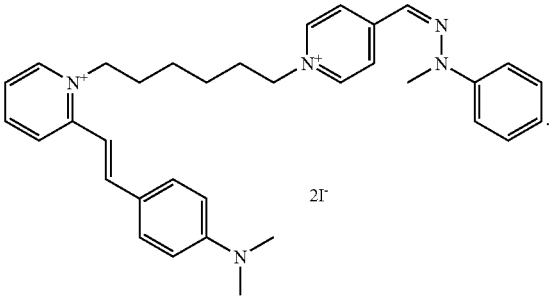

* * * * *